(12) United States Patent
Huang et al.

(10) Patent No.: US 10,829,734 B2
(45) Date of Patent: Nov. 10, 2020

(54) PREPARATION METHOD FOR OLFACTORY ENSHEATHING CELLS

(71) Applicant: BEIJING HONGTIANJI NEUROSCIENCE ACADEMY, Beijing (CN)

(72) Inventors: Hongyun Huang, Beijing (CN); Wenyong Gao, Beijing (CN); Juan Xiao, Beijing (CN)

(73) Assignee: BEIJING HONGTIANJI NEUROSCIENCE ACADEMY, Beijing (CN)

( * ) Notice: Subject to any disclaimer, the term of this patent is extended or adjusted under 35 U.S.C. 154(b) by 26 days.

(21) Appl. No.: 15/754,171

(22) PCT Filed: Aug. 11, 2016

(86) PCT No.: PCT/CN2016/094529
§ 371 (c)(1),
(2) Date: Feb. 21, 2018

(87) PCT Pub. No.: WO2017/032224
PCT Pub. Date: Mar. 2, 2017

(65) Prior Publication Data
US 2018/0245040 A1 Aug. 30, 2018

(30) Foreign Application Priority Data
Aug. 21, 2015 (CN) .......................... 2015 1 05160552

(51) Int. Cl.
*C12N 5/079* (2010.01)

(52) U.S. Cl.
CPC ........ *C12N 5/0622* (2013.01); *C12N 2500/02* (2013.01); *C12N 2501/11* (2013.01); *C12N 2501/115* (2013.01); *C12N 2501/999* (2013.01); *C12N 2509/00* (2013.01)

(58) Field of Classification Search
CPC .. C07K 14/47; C07K 16/241; C07K 14/4702; C07K 14/525; C07K 14/70575; C07K 16/18; C07K 2319/00; C07K 2319/02; C07K 2319/21; C07K 2319/30; C07K 2319/31; C07K 2319/42; A61K 38/00; A61K 48/00; A61K 38/1709; A61K 38/45; A61K 47/6425; A61K 47/6829; A61K 51/08; A61K 9/0024; A61K 9/19; A61K 2039/505; A61K 31/713; A61K 35/12; A61K 35/50; A61K 35/51; A61K 38/18; A61K 38/1808; A61K 38/1825; A61K 38/1833; A61K 38/1841; A61K 38/185; A61K 38/1858; A61K 38/1866; A61K 38/1891; A61K 38/19; A61K 38/204; A61K 38/2053; A61K 38/27; A61K 45/06; A61K 35/36; A61K 2035/124; A61K 35/30; A61K 35/74; A61K 35/744; A61K 35/747; Y02A 50/469; Y02A 50/412; A01N 1/0226; C12N 2500/32; C12N 2500/34; C12N 2500/44; C12N 2500/90; C12N 2500/95; C12N 2501/12; C12N 2501/21; C12N 2501/23; C12N 2502/02; C12N 2506/02; C12N 2506/03; C12N 2509/00; C12N 2509/10; C12N 2533/50; C12N 5/0605; C12N 5/0606; C12N 5/0607; C12N 5/06; C12N 9/00; C12N 2501/11; C12N 2501/115; C12N 2501/999; C12N 5/0622; C12N 15/113; C12N 2500/02; C12N 2501/40; C12N 2501/998; C12N 5/062; C12N 2500/38; C12N 2501/01; C12N 2501/119; C12N 2501/13; C12N 2501/135; C12N 2501/235; C12N 2501/41; C12N 2501/415; C12N 2506/097; C12N 2531/00; C12N 2533/52; C12N 2533/78; C12N 5/0619; C12N 1/18; C12N 1/20; C12N 2502/08; G01N 33/6884; G01N 2800/32; G01N 33/574; G01N 33/57423; Y10S 930/144; A01K 2217/05; A01K 2217/075; C07H 21/04; C12P 21/02; C12Q 1/68; C12Q 1/02; C12Q 1/6883; C12Q 2600/156; A61L 27/26; A61L 27/48; A61L 27/3804; A61L 27/3878; A61L 27/3895; C12R 1/225;
(Continued)

(56) References Cited

U.S. PATENT DOCUMENTS

2002/0127716 A1* 9/2002 Feron .................. C12N 5/0622
435/368

FOREIGN PATENT DOCUMENTS

| CN | 105062956 A | 11/2015 |
|----|-------------|---------|
| JP | 2007522796 A | 8/2007 |
| JP | 200753001 A | 11/2007 |

(Continued)

OTHER PUBLICATIONS

CN 101591641 A Abstract; Dec. 2009. Abstract Only. (Year: 2009).*
(Continued)

*Primary Examiner* — Deborah K Ware
(74) *Attorney, Agent, or Firm* — Cantor Colburn LLP

(57) ABSTRACT

Provided is a preparation method for olfactory ensheathing cells. The method comprises the steps of formulation of a cell medium, collection and pretreatment of tissues, enzymatic digestion, cell culture, cryopreservation, and differentiation culture. The prepared olfactory ensheathing cells can maintain the proliferative capacity for a long time, and still possess the activity of olfactory ensheathing cells after 11th passage.

24 Claims, 2 Drawing Sheets

(58) Field of Classification Search
CPC ... C12R 1/245; C12R 1/46; C08L 5/08; C08L 89/00; C12M 25/14
See application file for complete search history.

(56) References Cited

FOREIGN PATENT DOCUMENTS

| WO | 2001030982 A1 | 5/2001 |
|---|---|---|
| WO | 2004015102 A1 | 2/2004 |
| WO | 2007069927 A2 | 6/2007 |

OTHER PUBLICATIONS

Guest et al "Primate olfactory ensheating glia: anatomy, harvest methods, cutlure and characterization", Soc. for Neurosci. Abstracts, (2000), vol. 26, No. 1-2, pp. abstract only (Year: 2000).*

Ding, Dong et al.; "The Results of Olfactory Ensheathing Cells from Different Purification Methods", Progress in Modern Biomedicine, vol. 14, No. 19, Jul. 31, 2014.

Guo, Xin et al. "Comprison of Growth of Human Olfactory Epithelium Ensheathing Cells in Different Culture Conditions", Zhejiang Clinical Medical Journal vol. 16, No. 9; Sep. 30, 2014 .

Higginson et al. "The culture of olfactory ensheathing cells (OECs)—a distant glialn cell type" Institute of Infection, Immunity and Inflammation College of Medical, Veterinary & Life Sciences; journal homepage: www.elsevier.com/locate/yexnr (8 pages).

Jiang, Xiaorong et al.; "Isolation, Culture and Purification of Olfactory Ensheathing Cells from Huma Fetal Olfactory Mucosa"; Proceedings of the 5th Annual Conference of International Association of Neurorestoratology, The 9th Annual Conference of Global College of Neuroprotection & Neuroregeneration and the 4th International Spinal Cord Injury Treatments and Trials Symposium, Dec. 31, 2012 .

Nash et al. "New Method of Purification for Establishing Primary Cultures of Ensheathing Cells From the Adult Olfactory Bulb" Neuroscience Program (7 pages) .

Sheng, Weibin et al.; "Isolation, Culture and Identification of Olfactory Ensheathing Cells from Adult Rat Olfactory Mucosa"; Journal of Clinical Rehabilitative Tissue Engineering Research, vol. 12, No. 16, Apr. 15, 2008.

English Translation to Abstract for CN105062956.

International Search Report for Application No. PCT/CN2016/094529.

Au et al., "SPARC from Olfactory Ensheathing Cells Stimulates Schwann Cells to Promote Neurite Outgrowth and Enhances Spinal Cord Repair" The Journal of Neurosciences, vol. 27, No. 27, Jul. 4, 2007 (pp. 7208-7221).

Chang et al., "Primary Cultures and Immunocytochemical Observe of Olfactory Ensheathing Cells from Human Olfactory Mucosa", Orthopaedic Biomechanics Materials and Clinicals, vol. 5, Issue 4, Aug. 31, 2008, with English abstract (4 pages).

CN Office Action; CN Application No. 2015105160552; CN Filing Date Aug. 21, 2015 (with English translation, 2 pages).

European Search Report dated Dec. 14, 2018; EP Application No. 16838484.0; EP Filing Date Aug. 11, 2016 (10 pages).

Gu et al., "Conditioned medium of olfactory ensheathing cells promotes the funcitonal recovery and axonal regeneration after contusive spinal cord injury", Brain Research, Elsevier, vol. 1654, Oct. 24, 2016 (12 pages) .

Mayeur et al., "Potential of Olfactory Ensheathing Cells from Different Sources for Spinal Cord Repair" PLOS ONE, vol. 8, No. 4, Apr. 24, 2013 (12 pages).

Wang et al., "Isolationculture and Characteristics of Human Olfactory Mucosa Cells" ACTA Anatomica Sinica, vol. 41, Issue 3, Jun. 30, 2010 with English abstract (6 pages).

Watanabe et al., "Age-related changes in cell density and the proliferation rate of olfactory ensheathing cells in the lamina propria of postnatal mouse olfactory mucosa" Brain Research, Elsevier, vol. 1116, Oct. 20, 2006 (12 pages).

Zhang et al., "Influences of Human Serum and Nerve Grow Cells from Nasal Olfactorymucosa of Adult Human" Journal of Jiangsu University (Medicine Edition), vol. 17, Issue 1, Jan. 31, 2007 with English abstract (4 pages).

Feron, et al., "Autologous olfactory ensheathing cell transplantation in human spinal cord injury" Brain (2005) vol. 128 (pp. 2951-2960).

Richter, et al., "Culturing Olfactory Enshealing Cells from the Mouse Olfactory Epithelium" Methods in Molecular Biology, 2006, vol. 438 (pp. 96-102).

\* cited by examiner

PREPARATION METHOD FOR OLFACTORY ENSHEATHING CELLS

CROSS REFERENCE TO RELATED APPLICATIONS

This application is a National Stage of PCT Application No. PCT/CN2016/094529 filed on Aug. 11, 2016, which claims priority to Chinese Patent Application No. 2015105160552 filed on Aug. 21, 2015, the contents each of which are incorporated herein by reference thereto.

TECHNICAL FIELD

The present invention belongs to the field of cell culture technology, and relates to a preparation method for olfactory ensheathing cells comprising isolation, passage, cryopreservation and differentiation of olfactory ensheathing cells, and formulation of the required reagents.

BACKGROUND

Olfactory ensheathing cells (OECs), originating from olfactory epithelium, are dispersed in olfactory bulbs and olfactory mucosa. Primitive olfactory neurons, along with a large number of placode cells, migrate from efferent axons on olfactory mucosa towards telencephalic vesicles, and olfactory ensheathing cells guide olfactory neuronal axons to reach telencephalic vesicles. These cells form early olfactory bulbs which then evert, and the migrated cells cover their surfaces to form a thin layer, and then they penetrate glia limitan, resulting in the creation of olfactory nerve layer and glomerular layer, which become a new glia limitan covered the surfaces of olfactory bulbs. The olfactory ensheathing cells in an adult can still migrate through the glia limitan barrier between peripheral nerves and central nerves. In olfactory bulbs, olfactory ensheathing cells are the only glial cells which contact and surround olfactory neuronal axons. Throughout the whole central nervous system pathway, olfactory ensheathing cells surround olfactory neuronal axons to prevent their contact with the cells of other central nervous systems. OEC can secrete neurotrophic factors and substances for stimulating axon growth, which can promote axonal regeneration and facilitate myelination. As a type of special glial cells which have the similar functions with Schwann cells and oligodendrocytes, OEC has effects of nourishing, protecting, regulating or stimulating nerves, promoting myelination and axon regeneration, inhibiting glial hyperplasia and scar formation, and other repairing effects on nervous system. These properties of olfactory ensheathing cells provide a good internal environment for the functional and structural restoration and reconstruction of damaged or degenerative nerves. The properties of olfactory ensheathing cells make them the optimal option for nerurorestoration. The published articles regarding the transplantation of olfactory ensheathing cells have also powerfully demonstrated that olfactory ensheathing cells are the best cells for neurorestoration. However, the existing preparation method for olfactory ensheathing cells comprises: taking olfactory bulb tissues in the brain from aborted 3-5 months fetuses, culturing them directly with a certain amount of animal serum and then using a certain amount of cytarabine, physical methods or chemical agents to inhibit or reduce fibroblasts in order to achieve the purpose of purifying olfactory ensheathing cells. Use of a cryopreservation solution for olfactory ensheathing cells which is made by mixing animal serum in a high concentration with DMSO results in many disadvantages:

1. ethical factors: use of the olfactory bulb tissues which are derived from aborted fetuses may be constrained by ethics;

2. lower cell purity: (1) cytarabine and chemical reagents, which are broad-spectrum cytostatics, inhibit olfactory ensheathing cells while inhibiting growth of fibroblasts, and their amounts are difficult to be determined; (2) physical methods results in lost of a large number of olfactory ensheathing cells when removing fibroblasts; (3) fibroblasts grow faster and more easily when a serum-containing culture medium is used;

3. impossibility of continuous passage culture: (1) cytarabine and chemical reagents, as broad-spectrum cytostatics, affect the passage numbers of olfactory ensheathing cells; (2) when serum is used as a basic medium, olfactory ensheathing cells are easy to differentiate non-directionally and fibroblasts grow rapidly, and it is difficult to maintain biological characteristics after multiple passages;

4. existence of potential risks: allogeneic serum and tissue specimens are susceptible to viral and bacterial infections, and prone to result in rejections, allergies or other unknown dangers.

BRIEF SUMMARY

In order to solve the above mentioned problems existing in the prior art, the object of the present invention is to provide a preparation method that can obtain a large number of active olfactory ensheathing cells rapidly and conveniently, thereby providing a sufficient source of olfactory ensheathing cells for clinical neurorestoration treatment.

The technical solutions used to realize the above objects are as follows:

A preparation method for olfactory ensheathing cells, comprising the following steps:

(1) culturing single olfactory ensheathing cells derived from the olfactory mucosa of upper and middle turbinate in a culture medium for olfactory ensheathing cells under the condition of 37° C. and 5% $CO_2$, and allowing the cells grow adherently;

(2) mixing the cells obtained by filtering the culture supernatant obtained in step (1) with a culture medium for olfactory ensheathing cells again, culturing them under the condition of 37° C. and 5% $CO_2$, and allowing them grow adherently.

Preferably, the olfactory ensheathing cells are the olfactory ensheathing cells derived from human olfactory mucosa. Preferably, the culture medium for olfactory ensheathing cells is DMEM/DF12 (Gibco) as a basic medium, supplemented with the neurotrophic factors comprising 20-60 ng/ml EGF, 20-80 ng/ml FGF, 1-2 ml N2 (100×), 2-3 ml B27 (50×) and 0.1 μg/ml T3 (Sigma) at final concentrations.

Preferably, the culture medium for olfactory ensheathing cells derived from human olfactory mucosa is DMEM/DF 12 (Gibco), supplemented with the neurotrophic factors comprising 20 ng/ml EGF (Pepro Tech), 20 ng/ml FGF (Pepro Tech), 1% N2 (Gibco), 2% B27 (Gibco) and T3 (Sigma).

Preferably, the preparation method for single olfactory ensheathing cells comprises the following step:

digesting tissue blocks of the olfactory mucosa of upper and middle turbinate with an enzyme to obtain single cells.

More preferably, the preparation method for single olfactory ensheathing cells comprises the following step:

digesting tissue blocks of the olfactory mucosa of upper and middle turbinate with Collagenase I and a neutral protease to obtain single cells.

Preferably, the neutral protease is Dispase II for tissues.

More preferably, the preparation method for single olfactory ensheathing cells comprises the following step:

digesting tissue blocks of the olfactory mucosa of upper and middle turbinate in a size of 1 mm$^3$ with Collagenase I and a neutral protease in water bath at 37° C. under vibration, to obtain single cells, wherein the ratio by volume of the collagenase and neutral protease and the tissue blocks of olfactory mucosa of upper and middle turbinate is 2:1.

Preferably, Collagenase I is used at a concentration of 0.1% and the neutral protease is used at a concentration of 0.2%.

Further preferably, the tissue blocks of olfactory mucosa of upper and middle turbinate are washed before the digestion to remove residual blood on the surface; still further preferably, the residual blood on the surface is removed by a solution of penicillin and physiological saline in a ratio of 1:1; yet further preferably, the cleaned olfactory mucosa is cut into tissue blocks in a size of 1 mm$^3$ with a sterile scissor in a culture dish.

Preferably, the inoculation density of the culture in step (1) is 1×10$^4$ cells/ml. Preferably, the cells grow adherently to 90%.

Preferably, the inoculation density of the culture in step (2) is 1×10$^4$ cells/ml; Preferably, the cells grow adherently to 90%.

Preferably, the preparation method further comprises the steps of passage or cryopreservation of olfactory ensheathing cells.

More preferably, during the passage, the culture supernatant of the cells to be passaged is collected, filtrated and mixed with a culture medium for olfactory ensheathing cells from olfactory mucosa in a ratio of 1:3 to formulate a culture medium for passage.

Preferably, the preparation method further comprises a step of cryopreservation of olfactory ensheathing cells; preferably, the cryopreservation is the cryopreservation at an ultralow temperature; preferably, the cryopreservation of olfactory ensheathing cells at an ultralow temperature comprises the following steps: filtering the culture supernatant when the cells in step (2) grow adherently to 90%, and preparing a cryopreservation medium for olfactory ensheathing cells from the culture supernatant for cryopreservation. More preferably, the cryopreservation medium for olfactory ensheathing cells consists of the autologous serum, the culture supernatant, DMEM/F12 and DMSO. Further preferably, the cryopreservation medium for olfactory ensheathing cells consists of the autologous serum, the culture supernatant, DMEM/F12 and DMSO in a ratio by volume of 5:2:2:1.

Preferably, the preparation method further comprises a step of differentiation culture of olfactory ensheathing cells; preferably, the step of differentiation culture of olfactory ensheathing cells comprises adding a culture medium for differentiation of glial cells to the olfactory ensheathing cells for differentiation culture. More preferably, the culture medium for differentiation of glial cells consists of a culture medium for olfactory ensheathing cells and the autologous serum in a ratio by volume of 87:13.

In a specific embodiment of the present invention, the preparation method consists of:

Step 1. formulating a culture medium for olfactory ensheathing cells with neurotrophic factors;

Step 2. collection of tissues: gripping an appropriate amount of the olfactory mucosa tissues of upper and middle turbinate under local anesthesia;

Step 3. pretreatment of tissue blocks: washing the residual blood on the surfaces of gripped tissue blocks and processing the tissue blocks into ones in a size of 1 mm$^3$;

Step 4. digestion with a combination of two enzymes: collecting the scissor-minced tissue blocks, adding 2 volumes of Collagenase I and a neutral protease, and digesting in water bath at 37° C. under vibration;

Step 5. primary culture: collecting single cells obtained by the digestion and placing them in a centrifuge tube, mixing thoroughly with a culture medium for olfactory ensheathing cells, then inoculating in a cell culture flask, and culturing in an incubator at 37° C. and 5% $CO_2$;

Step 6. passage culture: collecting and filtering the culture supernatant of the cell to be passaged when the cells grow adherently to around 90%, and mixing it with a culture medium for olfactory ensheathing cells in a ratio of 1:3, to formulate a culture medium for the present passage.

Step 7. cryopreservation at an ultralow temperature: collecting and filtering the supernatant of the cells to be cryopreserved when the cells grow adherently to around 90%, to formulate a cryopreservation medium specific for olfactory ensheathing cells (comprising the autologous serum, the cell culture supernatant, DMEM/F12 and DMSO); and cryopreserving according to the routine procedures;

Step 8. differentiation culture: adding a formulated culture medium for differentiation of glial cells (a culture medium for olfactory ensheathing cells: the autologous serum=87:13), and differentiation culturing according to the routine procedures.

The preparation method of the present invention involves collection of tissues, digestion by a combination of two enzymes, passage culture, cryopreservation at an ultralow temperature, differentiation culture, and formulation of the required reagents. The advantages of the present invention are that the provided method for extracting and culturing olfactory ensheathing cells can rapidly obtain a large amount of olfactory ensheathing cells and maintain the proliferative capacity of the olfactory ensheathing cells for a long time, and the cells obtained after 11$^{th}$ passage still have the activities of olfactory ensheathing cells, as shown in the figures. FIG. 1 shows that the adherent cells are spindle-shaped, with bipolar elongated protuberances, tripolar elongated protuberances, or polygon, observed under an ordinary inverted microscope, magnification: 10×/0.25. FIG. 2 shows the results of immunohistochemical staining of olfactory ensheathing cells under a confocal microscope, wherein (A) shows green fluorescence, immunocytochemical staining for S100; (B) shows red fluorescence, immunocytochemical staining for p75 (L-NGFR); (C) shows blue fluorescence, with the nuclei being labeled by Hoechst; and (D) is a graph with full-spectrum fluorescence; magnification: 20×/0.5. The cultured cells express S100 and P75 (L-NGFR) in high levels, which are the positive markers of olfactory ensheathing cells.

DETAIL DESCRIPTION

Figure 1:
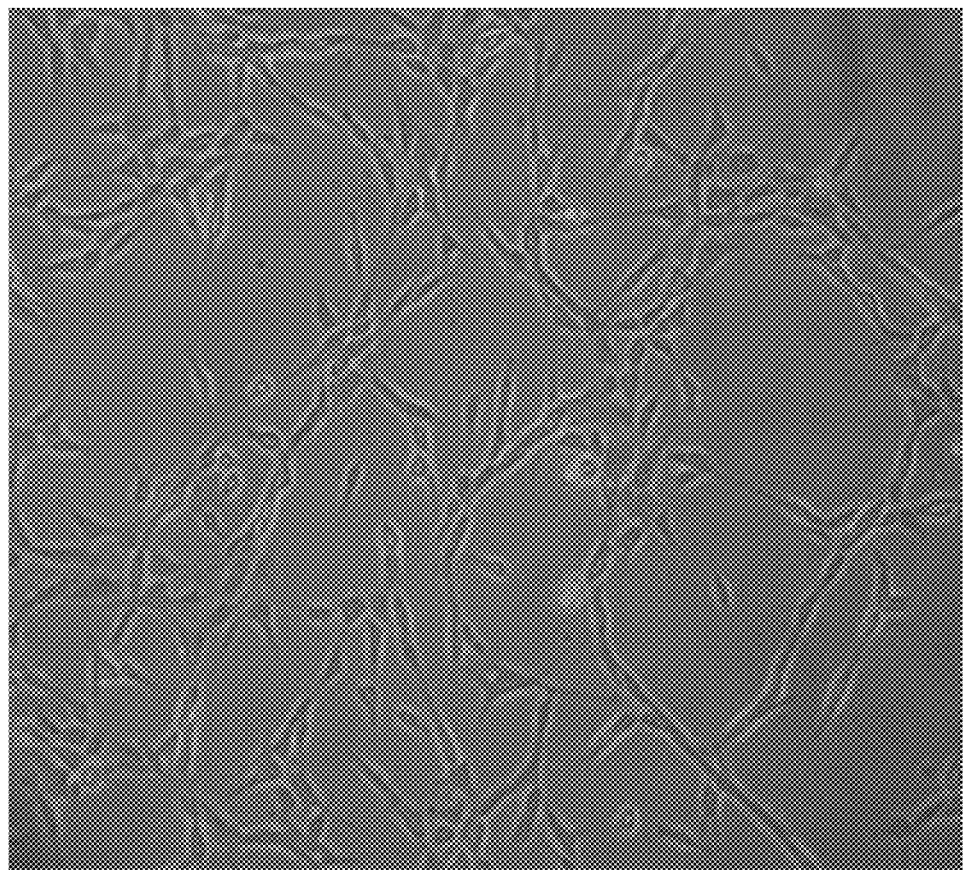
FIG. 1 shows the results of microscopy examination on the olfactory ensheathing cells, magnification: 10×/0.25.
Figure 2:
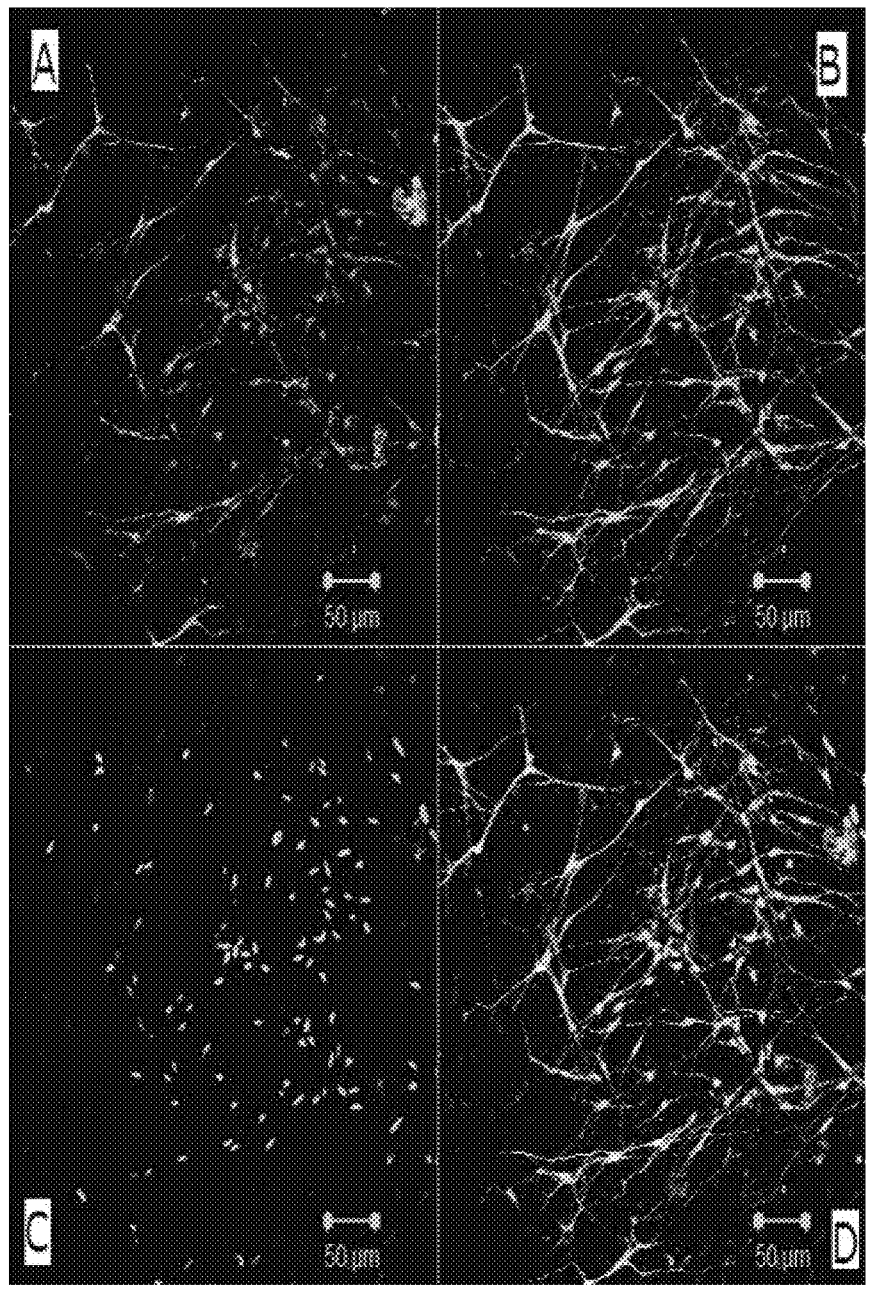
FIG. 2 shows the confocal microscopy identifications of the olfactory ensheathing cells using immunohistochemical staining, magnification: 20×/0.5.

1. Formulation of a Culture Medium for Olfactory Ensheathing Cells

A culture medium for olfactory ensheathing cells was formulated with DMEM/DF12 (Gibco) as a basic culture medium, which was supplemented with the culture factors comprising 20-60 ng/ml EGF, 20-80 ng/ml FGF, 1-2 ml N2 (100×), 2-3 ml B27 (50×) and 0.1 µg/ml T3 (Sigma) at final concentrations, then filtered and sterilized in a clean bench and stored at 4° C. for later use.

2. Collection of Tissues

Two days before the acquisition of tissue blocks, the nasal cavity was cleaned up and confirmed to be uninfected. Before the acquisition, two operations of local anaesthesia were performed intranasally by inserting a sheet of cotton yarn dipped with a physiological saline containing 1.2%-1.5% tetracaine into the nasal cavity with a gun-shaped forceps, each being performed for 5-10 min; the olfactory mucosa tissues close to the upper and outer ⅓ of upper and middle turbinate were taken with forceps for ethmoidal sinus, and the obtained tissues were placed into a glass dish; and then the glass dish was placed into an ice box, which was taken back to a culture room immediately.

3. Pretreatment of Tissues

After being taken back to the lab, the tissue blocks were washed with a physiological saline containing 100 U/ml penicillin to remove the residual blood on the surface of the mucosa tissue blocks, and cut into ones in a size of 1 mm$^3$ with a sterile ophthalmological scissors in a glass dish.

4. Digestion by a Combination of Two Enzymes

The scissor-minced tissue blocks were collected, to which added 2 volumes of Collagenase I and a neutral protease, and digested in water bath at 37° C. under vibration for 15 min, and then were pipetted repeatedly with a pipette having a thick elbow, and allowed to settle naturally for 1 min. The supernatant was transferred into a centrifuge tube and the digestion was terminated. The above operation was repeated 3 times so that the tissues could be digested into a single cell suspension. All the cell suspensions after the termination of digestion were collected together and centrifuged at 1200 r/4 min, washed with DMEM/F12 and centrifuged at 1200 r/4 min for a total of 3 times.

5. Primary Culture

A culture medium for olfactory ensheathing cells was added to prepare a single cell suspension, which was inoculated into a plastic culture flask with a bias opening treated by poly-L-lysine at a density of $1 \times 10^4$ cells/ml, then cultured in a constant temperature and humidity incubator at 37° C. and 5% $CO_2$.

6. Passage Culture

The supernatant of culture was collected when the cells grew to around 90% confluence, filtered with a 0.22 µm filter and mixed with a culture medium for olfactory ensheathing cells in a ratio of 1:3 to formulate the culture medium for the present passage; the cells was collected, to which added an appropriate amount of culture medium for passage to prepare a cell suspension, after staining with trypan blue, viable cells were counted under a microscope and then passaged again, with the density of the passaged cells being $1 \times 10^4$ cells/cm$^3$.

7. Cryopreservation at an Ultralow Temperature

The supernatant of culture was collected when the cells grew to around 90% confluence, filtered with a 0.22 µm filter to formulate a cryopreservation medium specific for olfactory ensheathing cells (a ratio by volume of the autologous serum:the supernatant of cell culture:DMEM/F12:DMSO=5:2:2:1); the cells for cryopreservation were collected routinely, to which added a cryoprotectant, and the final density of the cells was adjusted to $5 \times 10^6$ cells/ml~$5 \times 10^7$ cells/ml. The cells were stored at 4° C. for 60 minutes and at −20° C. for 70 minutes, and were cryopreserved at an ultralow temperature of −80° C. overnight before being placed in a liquid nitrogen tank.

8. Differentiation Culture

A differentiation medium for glial cells (a ratio by volume of a culture medium for olfactory ensheathing cells: the autologous serum=87:13) was formulated, and preserved at 4° C. for later use; the formulated differentiation medium for glial cells was added and a differentiation culture was carried out according to the routine procedures.

The present invention has been specifically described above with reference to the examples. However, the present invention is not limited to the above examples. Within the scope of the knowledge of those of ordinary skill in the art, various modifications may be made without departing from the spirit of the present invention, or the present invention can be applied directly or indirectly in other related technical fields, all of which are similarly included in the scope of the present invention.

The invention claimed is:

1. A preparation method for olfactory ensheathing cells, comprising the following steps:
   (1) culturing single olfactory ensheathing cells derived from the olfactory mucosa of upper and middle turbinate in a culture medium for olfactory ensheathing cells under the conditions of 37° C. and 5% $CO_2$, and allowing the single olfactory ensheathing cells to grow adherently;
   (2) mixing the cells obtained by filtering a culture supernatant obtained from step (1) with a culture medium for olfactory ensheathing cells, culturing under the conditions of 37° C. and 5% $CO_2$, and allowing the cells to grow adherently; and
   (3) passage culture of the cells,
   wherein the cells obtained still have the activities of olfactory ensheathing cells, after $11^{th}$ passage,
   wherein the culture medium for olfactory ensheathing cells is DMEM/DF12 (Gibco) as a basic culture medium, supplemented with the neurotrophic factors comprising 20-60 ng/ml EGF, 20-80 ng/ml FGF, 1-2 ml N2 (100×), 2-3 ml B27 (50×) and 0.1 µg/ml T3 (Sigma) at final concentrations.

2. The method according to claim 1, wherein the olfactory ensheathing cells are the olfactory ensheathing cells derived from human olfactory mucosa.

3. The method according to claim 1, wherein the preparation method for single olfactory ensheathing cells comprises the following step:
   digesting tissue blocks of the olfactory mucosa of upper and middle turbinate with an enzyme to obtain single cells.

4. The method according to claim 3, wherein the tissue blocks of the olfactory mucosa of upper and middle turbinate are washed before the digestion to remove the residual blood on the surface.

5. The method according to claim 1, wherein the innoculation density of the culture in step (1) is $1 \times 10^4$ cells/ml.

6. The method according to claim 1, wherein the preparation method further comprises a step of differentiation culture of the olfactory ensheathing cells.

7. The method according to claim 1, wherein the preparation method comprises the following steps:

Step 1. formulating a culture medium for olfactory ensheathing cell with neurotrophic factors;

Step 2. collection of tissues: picking up an appropriate amount of the olfactory mucosa tissues of upper and middle turbinate under local anesthesia;

Step 3. pretreatment of tissue blocks: washing the residual blood on the surface of the obtained tissue blocks and processing the tissue blocks into ones in a size of 1 mm$^3$;

Step 4. digestion by a combination of two enzymes: collecting the scissor-minced tissue blocks, adding 2 volumes of Collagenase I and a neutral protease, and digesting in water bath at 37° C. under vibration;

Step 5. primary culture: collecting the single olfactory ensheathing cells obtained by the digestion and placing them in a centrifuge tube, mixing thoroughly with a culture medium for olfactory ensheathing cells, then inoculating in a cell culture flask, and culturing in an incubator at 37° C. and 5% $CO_2$;

Step 6. passage culture: collecting a culture supernatant of the cells to be passaged when the cells grow adherently to around 90%, filtering and mixing the supernatant with a culture medium for olfactory ensheathing cells in a ratio of 1:3, to formulate a culture medium for the present passage;

Step 7. cryopreservation at an ultralow temperature: collecting and filtering a supernatant of cells to be cryopreserved when the cells grow adherently to around 90%, to formulate a cryopreservation medium specific for the olfactory ensheathing cells consisting of the autologous serum, the cell culture supernatant, DMEM/F12 and DMSO; and cryopreserving according to the routine procedures; and Step 8. differentiation culture: adding a formulated culture medium for the differentiation of glial cells, wherein the culture medium for olfactory ensheathing cells: the autologous serum=87:13, and culturing for differentiation according to the routine procedures.

8. The method according to claim 1, wherein the preparation method for single olfactory ensheathing cells comprises the following step:
digesting tissue blocks of the olfactory mucosa of upper and middle turbinate with Collagenase I and a neutral protease to obtain single cells.

9. The method according to claim 8, wherein the neutral protease is Dispase II for tissues.

10. The method according to claim 1, wherein the preparation method for single olfactory ensheathing cells comprises the following step:
digesting tissue blocks of the olfactory mucosa of upper and middle turbinate in a size of 1 mm$^3$ with Collagenase I and a neutral protease in water bath at 37° C. under vibration to obtain single cells, wherein the ratio by volume of Collagenase I and a neutral protease to the tissue blocks of the olfactory mucosa of upper and middle turbinate is 2:1.

11. The method according to claim 4, wherein the residual blood on the surface is removed by a solution of penicillin and a physiological saline in a ratio of 1:1.

12. The method according to claim 4, further comprising a step of cutting the olfactory mucosa into tissue blocks in a size of 1 mm$^3$ in a culture dish with a sterile scissor.

13. The method according to claim 5, wherein the cells grow adherently to 90%.

14. The method according to claim 1, wherein during the passage culture, the culture supernatant of the cells to be passaged is collected, filtrated and mixed with a culture medium for olfactory ensheathing cells from olfactory mucosa in a ratio of 1:3 to formulate a culture medium for passage.

15. The method according to claim 10, wherein Collagenase I is used at a concentration of 0.1% and the neutral protease is used at a concentration of 0.2%.

16. The method according to claim 1, wherein the innoculation density of the culture in step (2) is $1\times10^4$ cells/ml.

17. The method according to claim 16, wherein the cells grow adherently to 90%.

18. The method according to claim 1, wherein the preparation method further comprises a step of cryopreservation of the olfactory ensheathing cells.

19. The method according to claim 18, wherein the cryopreservation is cryopreservation at an ultralow temperature.

20. The method according to claim 19, wherein the cryopreservation of the olfactory ensheathing cells at an ultralow temperature comprises the following steps: filtering the culture supernatant when the cells in step (2) grow adherently to 90% to prepare a cryopreservation medium for the cryopreservation of olfactory ensheathing cells.

21. The method according to claim 20, wherein the cryopreservation medium for olfactory ensheathing cells consists of the autologous serum, the culture supernatant, DMEM/F12 and DMSO.

22. The method according to claim 20, wherein the cryopreservation medium for olfactory ensheathing cells consists of the autologous serum, the culture supernatant, DMEM/F12 and DMSO in a ratio by volume of 5:2:2:1.

23. The method according to claim 6, wherein the step of differentiation culture of the olfactory ensheathing cells comprises adding a culture medium for the differentiation of glial cells to the olfactory ensheathing cells and culturing for differentiation.

24. The method according to claim 23, wherein the culture medium for the differentiation of glial cells consists of a culture medium for olfactory ensheathing cells and the autologous serum in a ratio by volume of 87:13.

* * * * *